United States Patent [19]

Kato et al.

[11] 4,256,726

[45] Mar. 17, 1981

[54] $^{99m}$Tc-LABELED RADIOACTIVE DIAGNOSTIC AGENT, AND NON-RADIOACTIVE CARRIER THEREFOR

[75] Inventors: Makoto Kato; Masaaki Hazue, Mukomotomachi, both of Japan

[73] Assignee: Nihon Medi+Physics Co., Ltd., Hyogo, Japan

[21] Appl. No.: 901,605

[22] Filed: May 1, 1978

[30] Foreign Application Priority Data

May 7, 1977 [JP] Japan ................................. 52/52427

[51] Int. Cl.$^2$ ...................... A61K 29/00; A61K 43/00
[52] U.S. Cl. .......................................... 424/1; 424/2; 424/9
[58] Field of Search ..................................... 424/1, 9, 2

[56] References Cited

U.S. PATENT DOCUMENTS 3,981,980  9/1976  Baker et al. .............................. 424/1

OTHER PUBLICATIONS

Baker et al.; Journal of Nuclear Medicine, vol. 16, No. 8, 1975, pp. 720-727.
Kato et al.; Journal of Nuclear Medicine, vol. 19, No. 4, 1978, pp. 397-406.

*Primary Examiner*—Benjamin R. Padgett
*Assistant Examiner*—Christine M. Nucker
*Attorney, Agent, or Firm*—Birch, Stewart, Kolasch & Birch

[57] ABSTRACT

A $^{99m}$Tc-labeled radioactive diagnostic agent, prepared by contacting $^{99m}$Tc in the form of a pertechnetate with a non-radioactive carrier comprising pyridoxal or salt thereof, a stannous salt and an α-amino acid not having any hydrophilic functional group dissolved in an aqueous medium. This diagnostic agent is suitable for the examination of hepatobiliary ducts due to its smooth transfer through the hepatobiliary ducts as well as its high stability and non-toxicity.

6 Claims, No Drawings

$^{99m}$Tc-LABELED RADIOACTIVE DIAGNOSTIC AGENT, AND NON-RADIOACTIVE CARRIER THEREFOR

The present invention relates to a $^{99m}$Tc-labeled radioactive diagnostic agent and a non-radioactive carrier therefor. More particularly, it relates to a novel $^{99m}$Tc-labeled radioactive diagnostic agent which is useful for visualization and dynamic inspection of hepatobiliary ducts and having a high stability and no material toxicity, and a non-radioactive carrier therefor.

For the purpose of non-invasive, dynamic inspection of hepatobiliary ducts, there have been used $^{131}$I-labeled radioactive diagnostic agents such as $^{131}$I-labeled bromosulfophthalein and $^{131}$I-labeled Rose Bengal. However, $^{131}$I emits $\beta$-rays and has a long half life (i.e. about 8 days) so that those radioactive diagnostic agents result unfavorably in giving remarkable radiation exposure for patients.

Since $^{99m}$Tc emits only $\gamma$-rays of about 140 KeV and has a short half life (i.e. about 6 hours), it is quite suitable as a nucleus for radioactive diagnostic agents to be administered to human bodies. Because of this reason, attempts have been made to provide $^{99m}$Tc-labeled radioactive hepatobiliary diagnostic agents, of which examples are $^{99m}$Tc-penicillamine, $^{99m}$Tc-2-mercaptoisobutyric acid, $^{99m}$Tc-N-(2,6-dimethylphenylcarbamoylmethyl)iminodiacetic acid, etc. However, these conventional radioactive diagnostic agents are not satisfactory in their transfer rate from the liver into the gall bladder, their stability and toxicity, etc.

As the result of an extensive study to overcome the said drawbacks as seen in conventional $^{99m}$Tc-labeled radioactive diagnostic agents, it has been found that an aqueous solution comprising pyridoxal or a salt thereof, a stannous salt and an $\alpha$-amino acid not having any hydrophilic functional group is quite suitable as a carrier for $^{99m}$Tc, and a radioactive diagnostic agent obtained by contacting $^{99m}$Tc in the form of a pertechnetate with the acid carrier affords a $^{99m}$Tc-labeled radioactive diagnostic agent, which is highly stable and non-toxic and realizes the transfer of $^{99m}$Tc from the liver to the gall bladder with a satisfactory rate.

Accordingly, a basic object of the present invention is to provide a $^{99m}$Tc-labeled radioactive diagnostic agent for examination of hepatobiliary ducts. Another object of this invention is to provide a $^{99m}$Tc-labeled radioactive hepatobiliary diagnostic agent, which is highly stable and materially non-toxic. A further object of the invention is to provide a non-radioactive carrier for $^{99m}$Tc. These and other objects of the invention will be apparent to those skilled in the art from the foregoing and subsequent descriptions.

The non-radioactive carrier of the present invention comprises as the essential components at least one of pyridoxal and its salts, at least one of the stannous salts and at least one of the $\alpha$-amino acids not having a hydrophilic functional group dissolved in an aqueous medium.

As the salts of pyridoxal, there may be used salts with inorganic acids such as hydrochloric acid, nitric acid, sulfuric acid and phosphoric acid or with organic acids such as acetic acid and oxalic acid. The stannous salts mean the salts of the divalent tin ion (Sn++), of which examples are stannous halides (e.g. stannous chloride, stannous fluoride), stannous sulfate, stannous nitrate, stannous acetate, stannous citrate, etc. The $\alpha$-amino acids not having a hydrophilic functional group may be aliphatic or aromatic $\alpha$-amino acids not having any hydrophilic functional group other than one amino group and one carboxy group as the essential constituents of the $\alpha$-amino acids. What is meant by the term "hydrophilic functional group" is any functional group whose presence increases the water solubility of the original $\alpha$-amino acid. Examples of such hydrophilic functional group are carboxy, hydroxyl, mercapto, amino, etc. Accordingly, specific examples of the $\alpha$-amino acids not having any hydrophilic functional group are as follows: glycine, alanine, valine, leucine, isoleucine, phenylalanine, etc. These may be either originated from natural sources or synthesized artificially.

On preparation of the non-radioactive carrier of the invention, the said essential components may be mixed in an optional order. The pH of the non-radioactive carrier is not limitative, but it is preferred to adjust the pH within a range of about 8 to 9, for instance, by the use of an acid (e.g. hydrochloric acid) or an alkali (e.g. sodium hydroxide).

In addition to the said essential components, the non-radioactive carrier may include any conventional additive such as an antioxidant (e.g. ascorbic acid), an isotonization agent (e.g. sodium chloride) or a preservative (e.g. benzyl alcohol).

The molar ratio of pyridoxal or its salt and the $\alpha$-amino acid not having any hydrophilic functional group in the non-radioactive carrier is usually within a range of about 0.3 to 3, preferably about 1. The stannous salt may be used in a sufficient amount to reduce $^{99m}$Tc in the form of a pertechnetate present in the $^{99m}$Tc-labeled radioactive diagnostic agent prepared by the use of the non-radioactive carrier of the invention. When the stabilities of the non-radioactive carrier and the $^{99m}$Tc-labeled radioactive diagnostic agent as well as the toxicity of the stannous salt are taken into consideration, the stannous salt may be used in an amount of 0.001 to 1 mol per 1 mol of pyridoxal or its salt. The concentration of pyridoxal or its salt in the non-radioactive carrier is usually not less than about 20 mmol/liter insofar as it is dissolved to give a clear solution (e.g. not more than about 500 mmol/liter), preferably from about 80 to 100 mmol/liter.

For preparation of the $^{99m}$Tc-labeled radioactive diagnostic agent, $^{99m}$Tc in the form of a pertechnetate may be contacted with the non-radioactive carrier. $^{99m}$Tc in the form of pertechnetate is used normally in its aqueous solution, which may include additionally any conventional additive such as a preservative (e.g. benzyl alcohol) or an isotonization agent (e.g. sodium chloride). While the concentration of $^{99m}$Tc in the aqueous solution as the $^{99m}$Tc-labeled radioactive diagnostic agent is not particularly limited, it should have such a concentration as can afford a sufficient radioactivity concentration for diagnosis of hepatobiliary ducts, preferably from about 0.1 to 50 mCi in about 0.5 to 5.0 ml at the time of administration.

As the result of the combination of the non-radioactive carrier in an aqueous solution form with an aqueous solution comprising $^{99m}$Tc in the form of a pertechnetate, there is prepared the $^{99m}$Tc-labeled radioactive diagnostic agent in situ. In general, Sn++ ions form an insoluble colloidal substance in an alkaline aqueous solution, and $^{99m}$Tc labels this colloidal substance. In the present invention, the non-radioactive carrier is normally an aqueous solution of about 8 to 9 in pH; nevertheless, when contacted with $^{99m}$Tc, the production of any tin colloid labeled with $^{99m}$Tc is not recognized. This is probably due to the formation of a chelate compound between a Schiff base produced in the non-radioactive carrier and Sn$^{++}$ ions.

The non-radioactive carrier of the present invention has the following advantageous characteristics:

(1) The carrier is quite stable so that it can be stored for a long period of time after the preparation;
(2) The carrier can afford a $^{99m}$Tc-labeled radioactive diagnostic agent by a simple operation, for instance, by contacting an aqueous solution comprising $^{99m}$Tc in the form of a pertechnetate therewith;
(3) The carrier is materially non-toxic, etc.

Further, the $^{99m}$Tc-labeled radioactive diagnostic agent prepared by the use of such a carrier has the following meritorious features:

(a) The diagnostic agent is stable for a sufficiently long period of time after the preparation;
(b) The labeling efficiency of $^{99m}$Tc is extremely high (e.g. 98% or more);
(c) When intravenously administered, the diagnostic agent is smoothly taken into the liver, transferred to the gall bladder and then passed through the bile duct to the small intestine so that the inspection can be accomplished within a short period of time;
(d) The radiation exposure for patients is much reduced in comparison with $^{131}$I-labeled radioactive hepato-biliary diagnostic agents.
(e) The toxicity is quite low, etc.

The $^{99m}$Tc-labeled radioactive diagnostic agent may be administered to patients in an amount sufficient to produce radioactivity necessary for examination of hepatobiliary ducts by an appropriate route. For instance, the intravenous adminstration of the $^{99m}$Tc-labeled radioactive diagnostic agent of about 1 to 3 ml in volume having a radioactivity of about 1 to 5 mCi to a patient is quite suitable for hepatobiliary diagnosis.

Practical and presently preferred embodiments of the present invention are illustratively shown in the following Examples.

EXAMPLE 1

Preparation of a non-radioactive carrier by the use of pyridoxal hydrochloride, valine and stannous chloride (hereinafter referred to as "PVSnA"):

Nitrogen gas, sterilized by passing through a filter of 0.22 μm in pore size, was introduced into pyrogen-free sterile water to eliminate dissolved oxygen therefrom. Into the oxygen-free water (100 ml), pyridoxal hydrochloride (3665 mg; 18 mmol), anhydrous stannous chloride (15.2 mg; 0.08 mmol) and L(+)-ascorbic acid (70 mg; 0.4 mmol) were dissolved under sterile conditions in a nitrogen atmosphere to make a clear solution (hereinafter referred to as "solution (A)"). Separately, L-valine sodium salt (2504 mg; 18 mmol) and sodium hydroxide (720 mg; 18 mmol) as a pH regulator were dissolved into the said oxygen-free water (100 ml) under sterile conditions in a nitrogen atmosphere to make a clear solution (hereinafter referred to as "solution (B)"). The solutions (A) and (B) were mixed together in a nitrogen atmosphere to obtain a yellow solution of pH 8 to 9 useful as a non-radioactive carrier "PVSnA". The non-radioactive carrier "PVSnA" (2.2 ml) was filled in an ampoule through a filter of 0.22 μm in pore size in a nitrogen atmosphere and sealed.

EXAMPLE 2

(A) Preparation of a $^{99m}$Tc-labeled radioactive diagnostic agent using the non-radioactive carrier "PVSnA" (hereinafter referred to as "Tc-(PVSnA)"):

The non-radioactive carrier "PVSnA" (1.5 ml) obtained in Example 1 was mixed with a physiologically saline solution containing $^{99m}$Tc (5 mCi) in the form of sodium pertechnetate (1.5 ml), stirred well and allowed to stand for 30 minutes to make a $^{99m}$Tc-labeled radioactive diagnostic agent "Tc-(PVSnA)".

The $^{99m}$Tc-labeled radioactive diagnostic agent "Tc-(PVSnA)" as prepared above was subjected to thin layer chromatography using a silica gel thin layer plate and a mixture of 90% methanol and methyl ethyl ketone (1:1 by volume ratio) as a developing solvent. Scanning with a radiochromato-scanner revealed the presence of a single spot having radioactivity at Rf=0.83, and any other radioactive peak was not recognized. Since, in the above chromatography system, $^{99m}$Tc in the form of pertechnetate is to be developed to Rf=0.96 and a $^{99m}$Tc-labeled tin colloid is to be retained at the original point, the presence of a single radioactive spot at Rf=0.83 may mean that the labeling efficiency is 100%.

(B) Distribution of the $^{99m}$Tc-labeled radioactive diagnostic agent "Tc-(PVSnA)" in the organs of rats:

The $^{99m}$Tc-labeled radioactive diagnostic agent "Tc-(PVSnA)" (0.2 ml) was administered intravenously to S.D. (Sprague-Dawley) strain female rats. Five minutes or 1 hour after the administration, the animals were sacrified, and various organs were taken out and subjected to measurement of radioactivity. The results are shown in Table 1.

TABLE 1

Distribution of Tc-(PVSnA) in organs of rat (% to radioactivity administered)

| Organs | After administration | |
|---|---|---|
| | 5 minutes | 1 hour |
| Liver | 25.31 | 1.24 |
| Small intestine | 44.82 | 79.84 |
| Large intestine | 0.88 | 0.11 |
| Stomach | 0.97 | 0.28 |
| Spleen | 0.12 | 0.06 |
| Lung | 0.56 | 0.15 |
| Heart | 0.15 | 0.03 |
| Kidney | 2.70 | 0.90 |
| Blood (1 ml) | 0.58 | 0.08 |
| Carcass | 13.62 | 2.33 |
| Bladder | 7.30 | 14.67 |

The above results show that the $^{99m}$Tc-labeled radioactive diagnostic agent "Tc-(PVSnA)" is superior to any conventional radioactive diagnostic agent for examination of hepatobiliary ducts in its distribution figure.

EXAMPLE 3

Stability of the non-radioactive carrier "PVSnA":

The non-radioactive carrier "PVSnA" as prepared in Example 1 was stored at 4° to 10° C. for 50 or 100 days. By the use of the resulting non-radioactive carrier, a $^{99m}$Tc-labeled radioactive diagnostic agent "Tc-(PVSnA)" was prepared as in Example 2. The labeling efficiency was confirmed to be 100% in both cases (i.e. after 50 days storage and after 100 days storage). The distributions in the organs of rats when tested as in Example 2 are shown in Table 2 wherein the values indicate those 1 hour after the administration.

TABLE 2

Distribution of Tc-(PVSnA) in organs of rat (% to radioactivity administered)

| Organs | After preparation | |
|---|---|---|
| | 50 days | 100 days |
| Liver | 1.26 | 1.34 |
| Small intestine | 80.00 | 81.38 |
| Large intestine | 0.10 | 0.18 |
| Stomach | 0.29 | 0.04 |
| Spleen | 0.04 | 0.07 |
| Lung | 0.15 | 0.16 |
| Heart | 0.03 | 0.05 |
| Kidney | 0.90 | 0.70 |
| Blood (1 ml) | 0.07 | 0.08 |
| Carcass | 2.33 | 2.53 |
| Bladder | 14.67 | 12.63 |

From the above results, it is understood that the non-radioactive carrier "PVSnA" is stable even after the storage at 4° to 10° C. for a period of 100 days or more.

EXAMPLE 4

Stability of the $^{99m}$Tc-labeled radioactive diagnostic agent "Tc-(PVSnA)":

The $^{99m}$Tc-labeled radioactive diagnostic agent "Tc-(PVSnA)" as prepared in Example 2 was stored at room temperature for 24 or 48 hours after the preparation. Then, the distribution of the resulting diagnostic agent in the organs of rats was examined as in Example 2. The results are shown in Table 3 wherein the values indicate those 1 hour after the administration.

TABLE 3

Distribution of Tc-(PVSnA) in organs of rat (% to radioactivity administered)

| Organs | After preparation | |
|---|---|---|
| | 24 hours | 48 hours |
| Liver | 1.56 | 1.62 |
| Small intestine | 81.38 | 81.21 |
| Large intestine | 0.18 | 0.10 |
| Stomach | 0.04 | 0.05 |
| Spleen | 0.07 | 0.04 |
| Lung | 0.16 | 0.07 |
| Heart | 0.05 | 0.04 |
| Kidney | 0.70 | 0.98 |
| Blood (1 ml) | 0.08 | 0.10 |
| Carcass | 2.53 | 2.72 |
| Bladder | 12.63 | 13.98 |

From the above results, it is understood that the $^{99m}$Tc-labeled radioactive diagnostic agent "Tc-(PVSnA)" is stable even after being stored at room temperature for 48 hours or more. Since the half life of $^{99m}$Tc is about 6 hours, the assurance of the stability for a period of about 24 hours is sufficient for the practical use of the $^{99m}$Tc-labeled radioactive diagnostic agent.

EXAMPLE 5

Preparation of non-radioactive carriers using α-amino acids other than valine:

Nitrogen gas, sterilized by passing through a filter of 0.22 μm in pore size, was introduced into pyrogen-free sterile water to eliminate dissolved oxygen therefrom. Into the oxygen-free water (100 ml), pyridoxal hydrochloride (3665 mg; 18 mmol), anhydrous stannous chloride (15.2 mg; 0.08 mmol) and L(+)-ascorbic acid (70 mg; 0.4 mmol) were dissolved under sterile conditions in a nitrogen atmosphere to make a clear solution (hereinafter referred to as "solution (C)"). Separately, L-isoleucine sodium salt (2757 mg; 18 mmol) and sodium hydroxide (720 mg; 18 mmol) as a pH regulator were dissolved into the said oxygen-free water (100 ml) under sterile conditions in a nitrogen atmosphere to make a clear solution (hereinafter referred to as "solution (D)"). The solutions (C) and (D) were mixed together in a nitrogen atmosphere to obtain a yellow solution of pH 8 to 9 useful as a non-radioactive carrier "PISnA". The non-radioactive carrier "PISnA" (2.2 ml) was filled in an ampoule through a filter of 0.22 μm in pore size in a nitrogen atmosphere and sealed.

In the same manner as above but using L-leucine, L-alanine or L-phenylalanine in place of L-isoleucine, there were prepared non-radioactive carriers "PLSnA", "PASnA" and "PPSnA". These non-radioactive carriers were yellow solutions having a pH of 8 to 9.

EXAMPLE 6

(A) Preparation of $^{99m}$Tc-labeled radioactive diagnostic agents using the non-radioactive carriers obtained by the use of α-amino acids other than L-valine:

The non-radioactive carrier as obtained in Example 5 (1.5 ml) and a physiologically saline solution containing $^{99m}$Tc in the form of sodium pertechnetate (1.5 ml) were mixed together and allowed to stand for 30 minutes to make a $^{99m}$Tc-labeled radioactive diagnostic agent.

(B) The $^{99m}$Tc-labeled radioactive diagnostic agent as prepared above (0.2 ml) was itravenously administered to rats. One hour after the administration, the animals were sacrificed. Various organs were taken out and subjected to measurement of radioactivity as in Example 2. The results are shown in Table 4.

TABLE 4

Distribution of $^{99m}$Tc-labeled radioactive diagnostic agents in organs of rat (% to total radioactivity administered)

| Organs | Non-radioactive carrier | | | |
|---|---|---|---|---|
| | PISnA | PLSnA | PASnA | PPSnA |
| Liver | 0.91 | 1.72 | 2.20 | 16.27 |
| Small intestine | 80.55 | 78.59 | 48.80 | 70.55 |
| Large intestine | 0.12 | 0.12 | 0.14 | 0.13 |
| Stomach | 0.07 | 0.00 | 0.09 | 0.00 |
| Spleen | 0.00 | 0.02 | 0.04 | 0.00 |
| Lung | 0.02 | 0.12 | 0.28 | 0.21 |
| Heart | 0.00 | 0.02 | 0.10 | 0.01 |
| Kidney | 1.00 | 1.48 | 3.12 | 0.73 |
| Blood (1 ml) | 0.06 | 0.12 | 0.17 | 0.06 |
| Carcass | 2.10 | 3.58 | 7.17 | 2.42 |
| Bladder | 14.69 | 13.68 | 36.89 | 9.20 |

From the above results, it is understood that the $^{99m}$Tc-labeled radioactive diagnostic agents are all useful for examination of hepatobiliary ducts.

EXAMPLE 7

Stability of the non-radioactive carriers prepared by the use of α-amino acids other than L-valine:

In the same manner as in Example 3, the stability of the non-radioactive carriers prepared in Example 5 was examined. As the result, it was confirmed that they are stable even after being stored for a period of 100 days or more.

EXAMPLE 8

Stability of the $^{99m}$Tc-labeled radioactive diagnostic agents obtained using the non-radioactive carriers prepared by the use of α-amino acids other than L-valine:

In the same manner as in Example 4, the stability of the $^{99m}$Tc-labeled radioactive diagnostic agents prepared in Example 6 was examined. As the result, it was confirmed that they are stable even after being stored for a period of 48 hours or more.

EXAMPLE 9

Toxicity of $^{99m}$Tc-labeled radioactive diagnostic agents:

In the same manner as in Example 1 or 5 but using the materials other than water in amounts of 5 times greater, there were prepared non-radioactive carriers having 5 fold concentrations in comparison with the concentrations of the non-radioactive carriers as prepared in Example 1 or 5.

The resulting non-radioactive carrier was admixed with a physiologically saline solution containing $^{99m}$Tc somewhat decayed in radioactivity and in the form of sodium pertechnetate in a volume ratio of 1:1, and the resulting mixture was intravenously administered to groups consisting of 10 S.D. strain male rats, of 10 S.D. strain female rats and of 10 I.C.R. strain female mice at a dose of 1 ml per 100 g of bodyweight (corresponding to an amount of 1000 fold of the designed dose for human beings) as well as to groups consisting of 10 female guinea pigs and of 10 male rabbits at a dose of 0.5 ml per 100 g of bodyweight (corresponding to an amount of 500 fold of the designed dose to human beings). As a control, the same volume of a phyiologically saline solution as above was intravenously administered to the separate groups of the same animals as above.

All of the changes were recorded daily for the said duration. No significant difference was recognized between the drug administered groups and the control groups.

After 10 days from the administration, all the animals were sacrificed and subjected to observation for abnormality in various organs. But, no abnormality was seen in any of the animals.

From the above results, it may be said that the toxicity of the $^{99m}$Tc-labeled radioactive diagnostic agent of this invention is extremely low.

What is claimed is:

1. A non-radioactive carrier comprising pyridoxal or a salt thereof, a stannous salt and an α-amino acid not having any hydrophilic functional group dissolved in an aqueous medium.

2. The non-radioactive carrier according to claim 1, wherein the concentration of pyridoxal or its salt is not less than 20 mmol/liter.

3. The non-radioactive carrier according to claim 1, wherein the molar ratio of pyridoxal or its salt and the α-amino acid is from 0.3 to 3.

4. The non-radioactive carrier according to claim 1, wherein the stannous salt is used in an amount of 0.001 to 1 mol per 1 mol of pyridoxal or its salt.

5. A $^{99m}$Tc-labeled radioactive diagnostic agent which comprises $^{99m}$Tc in the form of a pertechnetate and a non-radioactive carrier comprising pyridoxal or a salt thereof, a stannous salt and an α-amino acid not having any hydrophilic functional group dissolved in an aqueous medium.

6. The $^{99m}$Tc-labeled radioactive diagnostic agent according to claim 5, prepared by contacting an aqueous solution containing $^{99m}$Tc, the radioactivity of which is 0.1 to 50 mCi in a volume of 0.5 to 5 ml of aqueous solution at the time of administration, in the form of a pertechnetate with a non-radioactive carrier comprising pyridoxal or a salt thereof, a stannous salt and an α-amino acid not having any hydrophilic functional group dissolved in an aqueous medium.

* * * * *